(12) United States Patent
Nakanishi

(10) Patent No.: US 6,894,774 B2
(45) Date of Patent: May 17, 2005

(54) METHOD OF DEFECT INSPECTION OF GRAYTONE MASK AND APPARATUS DOING THE SAME

(75) Inventor: Katsuhiko Nakanishi, Kumamoto (JP)

(73) Assignee: Hoya Corporation, Tokyo (JP)

( * ) Notice: Subject to any disclaimer, the term of this patent is extended or adjusted under 35 U.S.C. 154(b) by 421 days.

(21) Appl. No.: 10/107,819

(22) Filed: Mar. 28, 2002

(65) Prior Publication Data

US 2003/0030796 A1 Feb. 13, 2003

(30) Foreign Application Priority Data

Aug. 10, 2001 (JP) ..................................... P.2001-244071

(51) Int. Cl.⁷ .............................................. G01N 21/88
(52) U.S. Cl. .................................................. 356/237.5
(58) Field of Search .......................... 356/237.1–237.6, 356/239.1–239.8, 600–624

(56) References Cited

U.S. PATENT DOCUMENTS 4,559,603 A * 12/1985 Yoshikawa ..................... 716/5
4,902,899 A    2/1990 Lin et al.
6,674,522 B2 * 1/2004 Krantz et al. ............ 356/237.1

FOREIGN PATENT DOCUMENTS

| JP | 1-51825    | 11/1989 |
| JP | 2-210250   | 8/1990  |
| JP | 9-145629   | 6/1997  |
| JP | 9-292347   | 11/1997 |
| JP | 11-95410 A | 4/1999  |

* cited by examiner

Primary Examiner—Tu T. Nguyen
(74) Attorney, Agent, or Firm—Sughrue Mion, PLLC

(57) ABSTRACT

A method of defect inspection of a graytone mask having a opaque part, a transmission part and a graytone part aimed at selectively varying the thickness of a photoresist film by decreasing the amount of light transmitted through an area wherein the amount of light transmitted therethrough is regulated. The method is characterized in that a transmittance signal obtainable by scanning a pattern in the mask is employed and that thresholds 8a and 8b for extracting transmittance defects in the graytone part are provided with respect to the transmittance signal 7, whereby it is decided that the transmittance defect is produced in the graytone part in case where the transmission signals exceed the thresholds respectively.

12 Claims, 4 Drawing Sheets

METHOD OF DEFECT INSPECTION OF GRAYTONE MASK AND APPARATUS DOING THE SAME

BACKGROUND OF THE INVENTION

1. Field of the Invention

The present invention relates to a method of defect inspection of a graytone mask and a photomask including a microscopic pattern and an apparatus doing the same.

2. Description of the Related Art

In recent years, attempts have been made to reduce the number of mask sheets by using graytone masks in the field of large-sized LCD masks (as set forth in the monthly FPD Intelligence, May, 1999).

As shown in FIG. 6A, such a graytone mask has a opaque part 1, a transmission part 2 and a graytone part 3 on a transparent substrate. The graytone part 3 corresponds to an area in which a opaque pattern 3a of not exceeding the resolution limit of an exposure device for a large-sized LCD using the graytone mask is formed, for example, and is designed to selectively change the thickness of a photoresist film by decreasing the light transmitted through this area so as to decrease the amount of irradiation due to the area, 3b showing a microscopic transmission part of not exceeding the resolution limit of the exposure device in the graytone part 3. Normally, the opaque part 1 and the opaque pattern 3a are formed with films that are made of the same material such as chromium (Cr) or a chromium compound and have the same thickness. The transmission part 2 and the microscopic transmission part 3b are transparent substrate parts, each without having a opaque film on the transparent substrate.

The resolution limit of the exposure device for the large-sized LCD using the graytone mask is about 3 μm in the case of an exposure device of a stepper type and about 4 μm in the case of an exposure device of a mirror projection type. Consequently, the space width of a transmission part 3b in the graytone part 3 of FIG. 6A is set at less than 3 μm and the line width of the opaque pattern 3a of not exceeding the resolution limit of the exposure device is set at less than 3 μm, for example. When the exposure device for the large-sized LCD is used for light exposure, as the exposure light transmitted through the graytone part 3 as a whole is deficient in the amount of light exposure, positive photoresists are left on a substrate though the thickness of the positive photoresists exposed to light via the graytone part 3 solely decreases. More specifically, there arises a difference in solubility of resists in developing liquid between parts corresponding to the ordinary opaque part 1 and to the graytone part 3 because of difference in the amount of light exposure and this results in, as shown in FIG. 6B, making a part 1' corresponding to the ordinary opaque part 1 as thick as about 1.3 μm, making a part 3' corresponding to the graytone part 3 as thick as about 0.3 μm and making a part corresponding to the transmission part 2 a part 2' without resists, for example. A first etching of a substrate as a workpiece is carried out in the part 2' without the resists so as to remove the resists in the thin part 3' corresponding to the graytone part 3 by ashing and the like and by carrying out a second etching of this part, the etching process is performed with one sheet of mask instead of two sheets of masks as conventionally used in order to cut down the number of masks for use.

A conventional method of inspection of a mask having only opaque and transmission parts will now be described.

FIG. 9A shows a condition in which a clear defect 11 (pinhole) and a opaque defect 12 (spot) are produced in a opaque part 1 and a transmission part 2 respectively with both parts being scanned by one of the lenses (hereinafter called an upper lens) of a comparative inspection device as shown by an arrow.

FIG. 9B shows an amount-of-transmission signal 13 obtainable along the scanning line of the lens. The amount-of-transmission signal 13 is detected by a CCD line sensor disposed in each lens unit, for example. The level of the amount-of-transmission signal 13 is B in the opaque part 1 and W in the transmission part 2. The transmittance of the opaque part 1 is set at 0% and the transmittance of the transmission part 2 is set at 100%. The amount-of-transmission signal 13 is basically formed of a pattern edge line signal (pattern form signal) generated at the edge (boundary between the opaque part and the transmission part) of the pattern. In case where defects are produced, there appear a clear defect signal 11' generated in the opaque part 1 and a opaque defect signal 12' generated in the transmission part 2.

FIG. 9C shows an amount-of-transmission signal 13' obtainable by the other lens (hereinafter called a lower lens) in case where no defect is produced even in the same pattern as that of FIG. 9A.

FIG. 9D shows a difference signal 14 obtained by subtracting the amount-of-transmission signal (a different portion) obtained at each lens; more specifically, there is shown therein a difference signal obtained by subtracting the amount-of-transmission signal 13' of FIG. 9C from the amount-of-transmission signal 13 of FIG. 9B. In the difference signal 14, only defect signals 11' and 12' are extracted because a pattern edge line signal is removed from the amount-of-transmission signal of each lens.

FIG. 9E shows a condition in which with the setting of thresholds necessary for extracting defects in the opaque part 1 and the transmission part 2 in the difference signal 14 that has extracted only defect signals, the clear defect is detected by a plus-side threshold 15a and the opaque defect is detected by a minus-side threshold 15b. Although the detection sensitivity increases as the thresholds lower, the thresholds are needed to be set at a level on which no false defects are picked up.

In order to make sure that what kind of defect is produced in which one of the lenses, the signal of the upper lens is compared with that of the lower lens in an upper lens circuit (by subtracting the signal of the lower lens from that of the upper lens), for example, so as to detect clear and opaque defects in the upper lens because a defect signal appears on the plus side when the clear defect is produced in the opaque part 1 of the upper lens and because a defect signal appears on the minus side when the opaque defect is produced in the transmission part 2 of the upper lens (FIG. 9B-(5)). In the same way, the signal of the lower lens is compared with that of the upper lens in a lower lens circuit (by subtracting the signal of the upper lens from that of the lower lens), for example, so as to detect clear and opaque defects in the lower lens because a defect signal appears on the plus side when the clear defect is produced in the opaque part 1 of the lower lens and because a defect signal appears on the minus side when the opaque defect is produced in the transmission part 2 of the lower lens.

As the conventional comparative inspection device mentioned above is a device for inspecting a conventional mask only having a opaque and a transmission part, it is unfit for inspecting a graytone mask having a graytone part.

More specifically, the following problems develop in case where the conventional comparative inspection device is used for inspecting a graytone mask.

As the defect signal in the graytone part is weak since the defect itself is very small and when the conventional comparative inspection device is employed, it is difficult to make defect inspection unless the threshold is set lower than a threshold normally used to inspect the opaque part. However, in case where the graytone part is an area wherein a microscopic pattern of not exceeding the resolution limit of the exposure device using the graytone mask, for example, a base signal level 16 (noise band) characteristic of the graytone part as shown in FIG. 5 is generated as what corresponds to the microscopic pattern. In making the comparative inspection, though only a defect signal is extracted by obtaining a difference signal after subtracting the amount-of-transmission signal (a different portion) obtained at each lens, the base signal level is amplified (by maximum two folds) when as light pattern shift is generated between the microscopic opaque patterns in the graytone part and a defect (false defect) that should not originally be treated as a defect comes to be detected; consequently, the threshold becomes impossible to lower and the problem is that high-sensitivity inspection cannot be fulfilled.

Further, as the comparative inspection conventionally carried out is intended to inspect clear and opaque defects, it remains difficult to ensure a transmittance as the most important factor in the graytone mask. In other words, in case where the line width of a opaque pattern in a graytone part is too large or too small as compared with a designed dimension, thus making the transmittance exceed the allowed value over the whole mask area and in case where the transmittance of a translucent film forming the graytone part exceeds the allowed value, for example, as the difference signal obtained by subtracting the amount-of-transmission signal of each lens in the comparative inspection, there is also a problem arising from making the transmittance undetectable because the difference will not appear. This is particularly problematical in that no form defect exists in the graytone part. Further, though the transmittance of the graytone part need not be detected as a defect as long as the transmittance thereof remains in the allowable range, since even the transmittance thereof within that allowable range is still detected in the conventional comparative inspection, there may be a case where the transmittance thereof thus detected remains in the allowable range. As a result, there is still a problem developed from failing to maintain inspection accuracy (capability) as what has originally been unnecessary to detect as a defect is subjected to detection.

There is additionally caused a similar problem to a photomask having a microscopic pattern such as a photomask for forming a TFT channel, for example. In the case of such a photomask for forming the TFT channel, for example, with the progress of rendering the TFT channel portion microscopic, the tendency is for the pattern to be rapidly made microscopic. In the case of even a pattern like this, there occur a false defect due to the vibration of the stage of the inspection device and a shift between the upper and lower lenses and any other false defect characteristic of the microscopic pattern when the inspection is carried out through the conventional method; the problem in this case is that a sensitivity at a level ensuring the defect detection is not secured when the sensitivity is lowered up to the level at which the false defect is not detected.

SUMMARY OF THE INVENTION

An object of the invention made to solve the foregoing problems is to provide a method of defect inspection capable of not only ensuring a transmittance but also carrying out high-sensitive defect inspection by preventing the detection of such form defects as false defects and as those whose transmittance is in an allowable range.

The following arrangements are made according to the invention.

(Arrangement 1) A method of defect inspection of a graytone mask having a opaque part, a transmission part and a graytone part aimed at selectively varying the thickness of a photoresist film by decreasing the amount of light transmitted through an area wherein the amount of light transmitted therethrough is regulated, the method being characterized in that a transmittance signal obtainable by scanning a pattern in the mask is employed and that thresholds for extracting transmittance defects in the graytone part are provided with respect to the transmittance signal, whereby it is decided that the transmittance defect is produced in the graytone part in case where the transmission signals exceed the thresholds respectively.

(Arrangement 2) A method of defect inspection as described in Arrangement 1 is characterized in that thresholds are further provided for extracting transmittance defects in the respective opaque and transmission parts, whereby it is decided that the transmittance defect is produced in the opaque or transmission part in case where each transmission signal exceeds each threshold.

(Arrangement 3) A method of defect inspection as described in Arrangement 1 is characterized in that the graytone part is an area wherein a opaque pattern of not exceeding the resolution limit of an exposure device using the graytone mask is formed and that the threshold for extracting the transmittance defect is set at a level exceeding a base signal level characteristic of the graytone part and also at a level exceeding an allowed amount of transmission in the graytone part.

(Arrangement 4) A method of defect inspection as described in Arrangement 1 is characterized in that the graytone part is an area wherein a translucent film capable of controlling the amount of light transmitted through the film is formed and that the threshold for extracting the transmittance defect is set at a level exceeding an allowable amount of transmission in the graytone part.

(Arrangement 5) An apparatus for defect inspection of a graytone mask having a opaque part, a transmission part and a graytone part aimed at selectively varying the thickness of a photoresist film by decreasing the amount of light transmitted through an area wherein the amount of light transmitted therethrough is regulated, the apparatus comprising:

means for detecting a transmittance signal by scanning a pattern formed in the mask with parallel light sources and light receiving lenses, means for setting a threshold for extracting a transmittance defect in at least the graytone part with respect to the transmittance signal, and means for deciding that the transmittance defect is produced in the graytone part in case where the transmission signal exceeds the threshold.

(Arrangement 6) A method of defect inspection as described in Arrangement 1 is characterized in that the graytone mask is a mask for producing an LCD or a mask for producing a display device.

(Arrangement 7) A method of defect inspection of a photomask is characterized in that a pattern defect in the photomask is detected from the abnormal fluctuation of transmittance based on a transmittance signal obtainable by scanning the pattern in the mask.

(Arrangement 8) A method of defect inspection of a photomask as described in Arrangement 7 is characterized in that the detection of the defect from the abnormal fluctuation of transmittance is based on the transmittance-defect threshold set in accordance with a pattern area as an object for inspection.

(Arrangement 9) A method of defect inspection of a photomask as described in Arrangement 7 is characterized in that the photomask is a mask containing a microscopic pattern for producing an LCD or a mask containing a microscopic pattern for producing a display device.

(Arrangement 10) An apparatus for defect inspection of a photomask, comprises:

means for detecting a transmittance signal by scanning a pattern formed in the mask with parallel light sources and light receiving lenses, means for setting a threshold for extracting a transmittance defect in accordance with a pattern area as an object for inspection with respect to the transmittance signal, and means for deciding that the transmittance defect is produced in the pattern area in case where the transmission signal exceeds the threshold.

BRIEF DESCRIPTION OF THE DRAWINGS

FIG. 6A is a partial plan view; and FIG. 6B, a partial sectional view.

DESCRIPTION OF THE PREFERRED EMBODIMENTS

According to Arrangements 1 and 5, the transmittance signal obtained by scanning the pattern in the mask is employed and the thresholds for extracting the transmittance defects in the graytone part are provided with respect to the transmittance signal, whereby the transmittance itself can directly be inspected to ensure the transmittance in the graytone part.

Moreover, as this is an inspection method without pattern recognition, a problem arising from the generation of a false defect originating from the pattern form characteristic of the microscopic pattern being subjected to inspection (a problem of allowing the threshold not to be lowered) can be avoided. Consequently, the threshold can be lowered, so that sensitivity satisfying the required precision (specification) of the graytone mask is obtainable.

The use of the transmittance signal makes it possible to avoid another problem of amplification of the base signal level characteristic of the graytone part (a problem of allowing the threshold not to be lowered) resulting from calculating a difference signal in the comparative inspection. Consequently, the threshold can be lowered, so that sensitivity satisfying the required precision of the graytone mask is obtainable.

Further, as no object for comparison is needed, monocular inspection is possible.

The threshold for extracting the transmittance defect in the graytone part is set changeable to ensure the transmittance in conformity with the light exposure conditions of the graytone mask used by a user.

According to Arrangement 2, the transmittance defects of translucency (so-called half condition) such as a defect resulting from the lowering of the opaque property of the opaque part and that of transmitting property of the transmission part are simultaneously made detectable. However, as the presence of the clear defect in the opaque part and that of the opaque defect in the transmission part do not means the presence of any abnormal transmittance, the transmission part and the opaque part are judged to be normal.

According to Arrangement 2, moreover, the use of the transmittance defect region formed by the threshold for extracting the transmittance defect in the graytone part together with the thresholds for extracting the transmittance defects in the normal opaque and transmission parts makes possible the detection of the transmittance defects without relying on the inspection area. In other words, the presence of the transmittance defect can be decided without relying on the inspection area provided that the inspection area is within the transmittance defect region.

Figure 5:
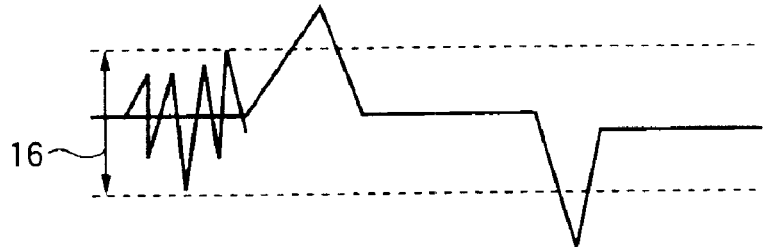
FIG. 5 is a drawing illustrating a base signal level characteristic of a graytone part.
Figure 6A:
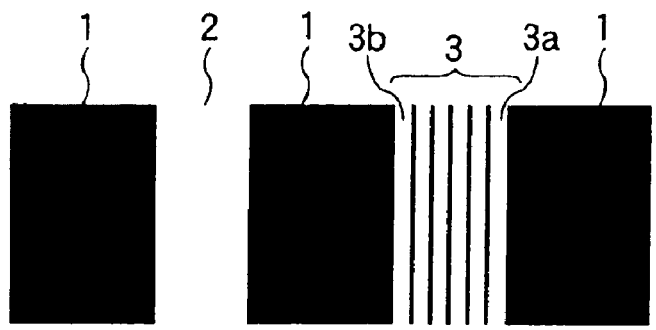
FIG. 6A and FIG. 6B are drawings illustrating a graytone mask.
Figure 6B:
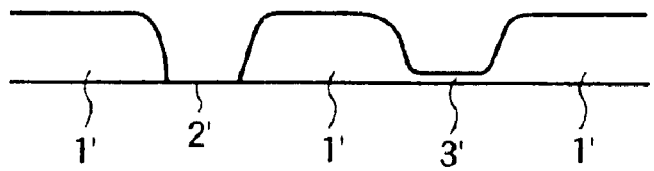

According to Arrangement 3, when the graytone part is an area wherein the opaque pattern of not exceeding the resolution limit of the exposure device using the graytone mask is formed, the threshold for extracting the transmittance defect is set at a level exceeding a base signal level 16 characteristic of the graytone part as shown in FIG. 5, whereby the influence of the base signal level characteristic of the graytone part can be eliminated. In this case, the threshold for extracting the transmittance defect is preferably set with the central value of the base signal level 16 as a reference. Moreover, the transmittance of the graytone part can be ensured by setting the threshold for extracting the transmittance defect at the upper limit and lower limit of the allowed transmittance of the graytone part.

According to Arrangement 4, when the graytone part is an area wherein the translucent film capable of controlling the amount of light transmitted through the film is formed, the transmittance of the graytone part can be ensured by setting the threshold for extracting the transmittance defect at the upper and lower limits of the allowed transmittance of the graytone part.

According to Arrangement 6, though a transmittance inspecting device integrally arranged with a microscope may be used to inspect the transmittance of the graytone part since the semiconductor graytone mask is normally small in size in spite of the fact that trouble and time are required to a certain degree, this method of inspection is not readily applicable to the graytone mask for producing the LCD as the processing burden is extremely heavy since the graytone mask is large in size and has many transmittance defects. Therefore, the defect inspection method according to the invention is indispensable for making graytone masks for producing LCDs fit for practical use.

This is also the case with not only masks for producing LCDs (Liquid Crystal Displays) but also masks for producing display devices. Masks for producing LCDs include all masks necessary for producing LCDs such as those for producing TFTs (Thin Film Transistors), low-temperature polysilicon TFTs, color filters and so forth. On the other hand, masks for producing display devices include those for producing organic EL (Electronic Luminescence) displays, plasma displays and so on.

According to Arrangements 7 to 10, the inspection methods described therein are those carried out without pattern recognition as the pattern defect is detected from the abnormal fluctuation of transmittance based on the transmittance signal obtained by scanning the pattern in the mask. Particularly, the problem arising from the generation of a false defect originating from the pattern form characteristic of the microscopic pattern being subjected to inspection (the problem of allowing the threshold not to be lowered) can be avoided. Consequently, the threshold can be lowered, so that sensitivity satisfying the required precision (specification) of the graytone mask is obtainable.

Moreover, the use of the transmittance signal makes it possible to avoid the problem of amplification of the base signal level characteristic of the graytone part (the problem of allowing the threshold not to be lowered) resulting from calculating the difference signal in the comparative inspection. Consequently, the threshold can be lowered, so that sensitivity satisfying the required precision of the graytone mask is obtainable.

As no object for comparison is needed, monocular inspection is possible.

Masks containing microscopic patterns as mentioned above include photomasks for producing LCDs and those for producing display devices such as organic EL displays and plasma displays, for example, photomasks having microscopic patterns for producing TFT channel parts and contact hole parts.

A description will now specifically be given of a method of defect inspection of a graytone mask having a graytone part and an apparatus therefor.

Figure 1A:
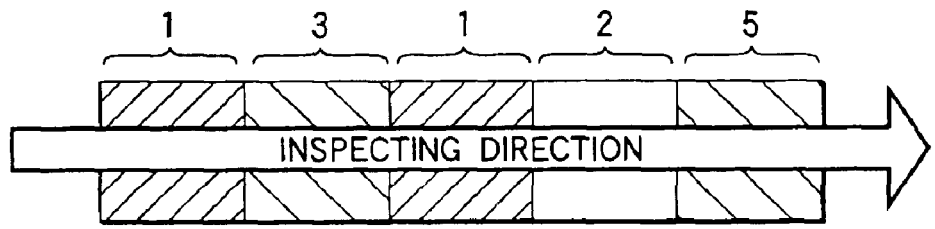
FIG. 1A and FIG. 1B are drawings illustrating a method of defect inspection embodying the invention.

FIG. 1A shows a condition in which no defect is produced in a opaque part 1, a transmission part 2, a graytone part 3 and a graytone part 5 with an arrow showing the scanning direction (inspecting direction) of lenses of an inspecting apparatus.

Figure 1B:
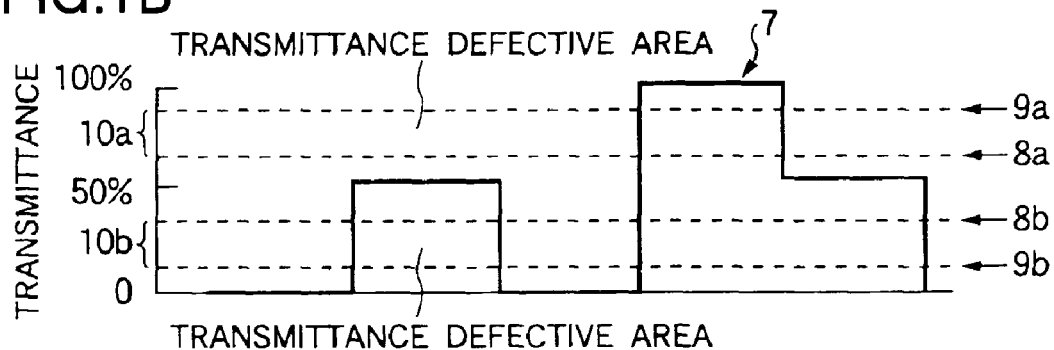

FIG. 1B shows an amount-of-transmission signal 7 obtainable along the scanning direction. The amount-of-transmission signal has a transmittance of 0% in the opaque part 1, a transmittance of 100% in the transmission part 2 and a transmittance of 50% in the graytone parts 3 and 5.

The invention is characterized by providing a fixed threshold to the amount-of-transmission signal so as to detect a transmittance defect.

More specifically, thresholds for extracting a transmittance defect in the graytone part are provided (on the upper limit side 8a and the lower limit side 8b) as shown in FIG. 1B and it is decided that a transmittance defect is produced in the graytone part when the threshold exceeds either of the threshold limits.

In this case, thresholds for extracting transmittance defects in the normal opaque and transmission parts are preferably provided (on the transmission part side 9a and the opaque part side 9b) as shown in FIG. 1B and it is decided that a transmittance defect is produced in the opaque part or the transmission part when the threshold exceeds either of the threshold limits whereby to simultaneously detect translucent transmittance defects such as a defect resulting from the lowering of the opaque property of the opaque part and that of transmitting property of the transmission part.

In this case, further, a transmittance defect can be detected without relying on the inspecting area by using transmittance defect regions 10a and 10b formed with transmittance-defect extracting thresholds 8a and 8b for the graytone part and transmittance-defect extracting thresholds 9a and 9b in the normal opaque and transmission parts. In other words, it is decided that such a transmittance defect is produced without relying on the inspecting on the inspecting area in case where the defects exist in the transmittance defect regions 10a and 10b.

The mode of the transmittance defect will not be described.

Figure 2A:
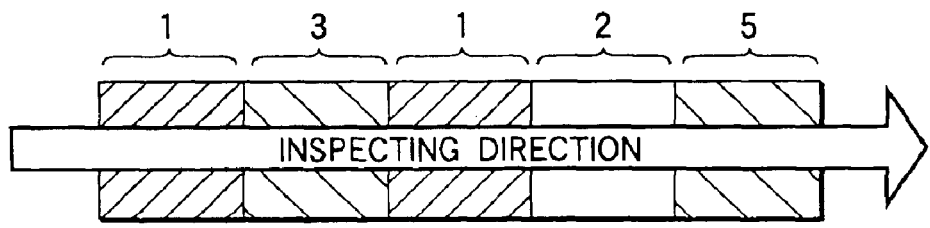
FIG. 2A and FIG. 2B are drawings illustrating one form of a transmittance defect.
Figure 2B:
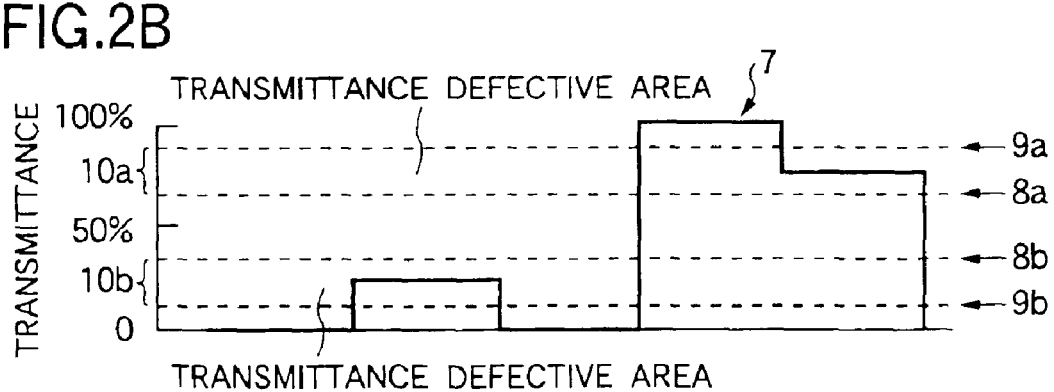

As shown in FIG. 2A, firstly, even in the absence of form defects (clear and opaque defects) in the graytone parts 3 and 5, the transmittance level of the whole graytone part may uniformly exceeds the transmittance defect thresholds (on the upper and lower limit sides 8a and 8b) as shown in FIG. 2B. According to the invention, the transmittance defect can be detected even in the absence of form defects in the graytone part. In such a case as this, the detection of the transmittance defect is made difficult by the comparative inspection.

Figure 3A:
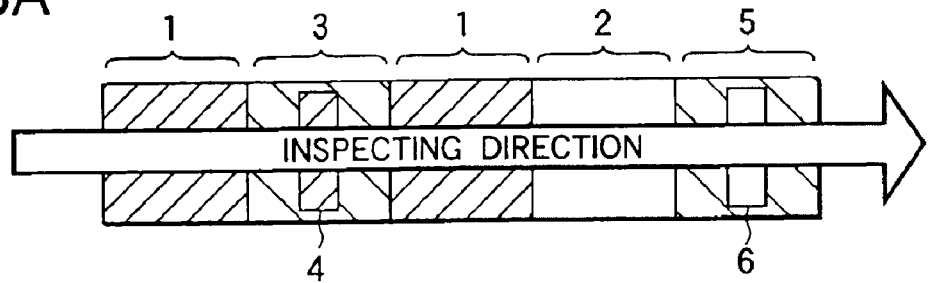
FIG. 3A and FIG. 3B are drawings illustrating another form of a transmittance defect.
Figure 3B:
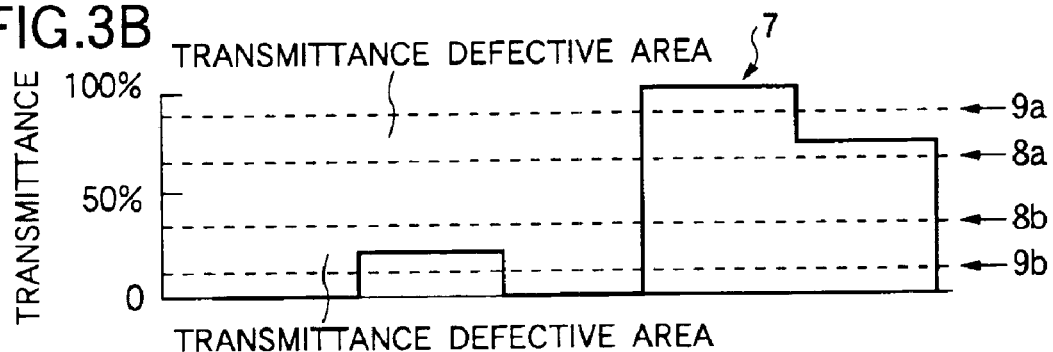

As shown in FIG. 3A, secondly, even in the presence of form defects (opaque and clear defects 4 and 6) in the graytone parts 3 and 5, the transmittance level of the whole graytone part may uniformly varies as shown in FIG. 3B, depending of the form defect. Even in this case, the transmittance defect can be detected according to the invention.

Figure 4A:
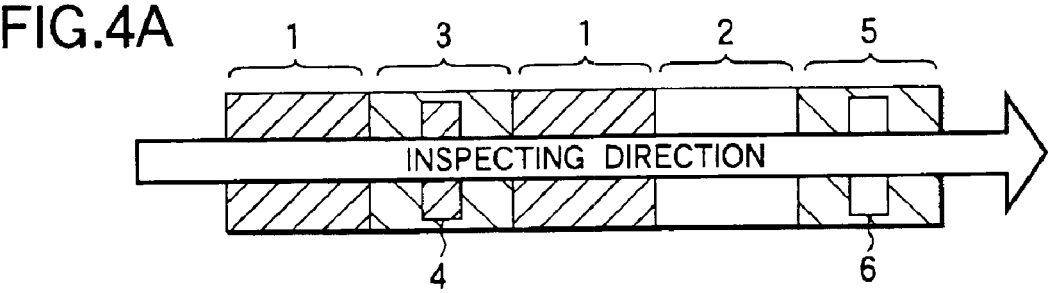
FIG. 4A and FIG. 4B are drawings illustrating still another form of a transmittance defect.
Figure 4B:
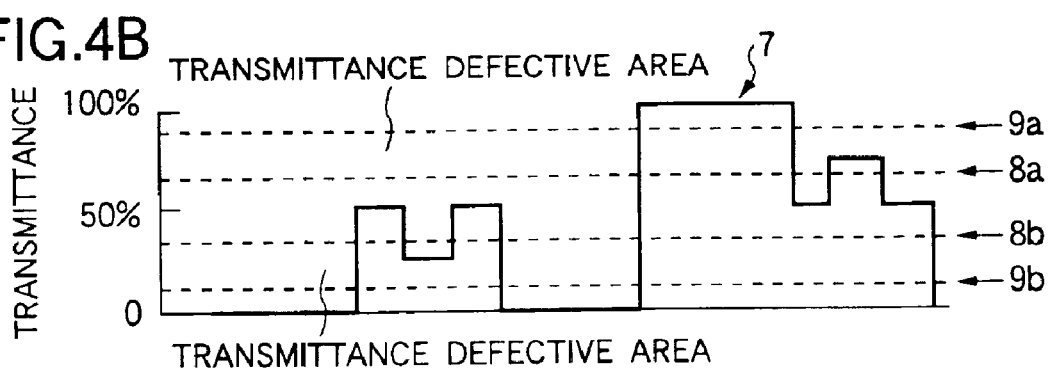

As shown in FIG. 4A, thirdly, in the presence of form defects (opaque and clear defects 4 and 6) in the graytone parts 3 and 5, a transmittance change may steeply appear in only a part where the form defect exists as shown in FIG. 4B because of the form defect. In such a case as this, the form defect in the graytone part can be detected as a transmittance defect.

According to the invention, when the graytone part is an area wherein the opaque pattern of not exceeding the resolution limit of the exposure device using the graytone mask is formed, the threshold for extracting the transmittance defect is set at a level exceeding a base signal level 16 characteristic of the graytone part as shown in FIG. 5, whereby the influence of the base signal level characteristic of the graytone part can be eliminated. In this case, the threshold for extracting the transmittance defect is preferably set with the central value of the base signal level 16 as a reference. Moreover, the transmittance of the graytone part can be ensured by setting the threshold for extracting the transmittance defect at the upper limit and lower limit (on the upper and lower limit sides 8a and 8b) of the allowed transmittance of the graytone part.

According to the invention, each threshold can be set to any given value. Particularly, the threshold for extracting the transmittance defect in the graytone part is set changeable to ensure the transmittance in conformity with the light exposure conditions of the graytone mask used by the user.

According to the invention, the transmittance inspection can be carried out for a graytone mask having only a graytone part and the transmittance inspection can also be carried out in case where a normal mask only comprising a opaque part and a transmission part is intermixed with a graytone mask having a opaque part, a transmission part and a graytone part.

A comparative inspection device according to the invention will now be described.

The comparative inspection device according to the invention has a means for detecting a transmittance signal by scanning a pattern formed in a mask with parallel light sources and light receiving lenses. More specifically, the comparative inspection device has, for example, the parallel light sources (spot light sources corresponding to the respective lenses or a light source for irradiating the whole surface of the mask) provided on one side of the mask, and two lenses provided on the other side of the mask and a means for scanning the whole mask area by relatively moving the mask and the lenses (normally, mask stage moving means), whereby the light transmitted therethrough is received by the lenses along the scanning direction. Further, a CCD line sensor disposed in a lens unit, for example, is used to detect the transmittance signal.

The transmittance signal is sent to a defect detection circuit having the threshold for extracting the transmittance defect in the graytone part and the threshold for extracting the transmittance defect in an ordinary part whereby to decide transmittance defects. When the transmittance signal having a transmittance in the intermediate transmittance region for a fixed time exceeds the upper or lower limit of the threshold for extracting the transmittance defect for the graytone part, the transmittance defect is decided in the defect detection circuit. In case where the transmittance signal situated near the transmittance of 0% for a fixed time is higher than the transmittance for extracting the transmittance defect for the opaque part, moreover, a transmittance defect is decided to exist in the opaque part. Similarly, in case where the transmittance signal situated near the transmittance of 100% for a fixed time is lower than the transmittance for extracting the transmittance defect for the opaque part, moreover, a transmittance defect is decided to exist in the transmission part. In these cases, an edge signal is never judged as a transmittance defect. Further, the threshold employed for detection can be used to determine the area wherein the defect is produced.

Incidentally, a means for identifying the area being subjected to inspection between the opaque and transmission parts and the graytone part may be provided according to the invention whereby to identify easily and surely the area wherein the transmittance defect is produced.

However, the invention is not limited to the above-described embodiment thereof.

Figure 7:
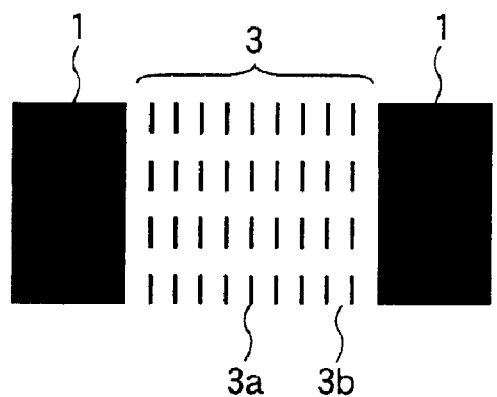
FIG. 7 is a partial plan view illustrating another aspect of the graytone part.
Figure 8:
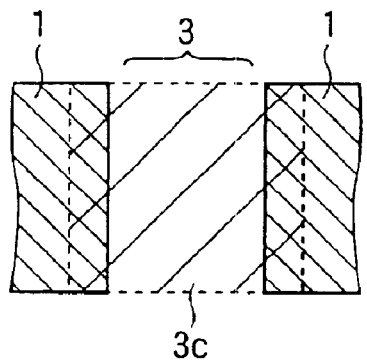
FIG. 8 is a partial plan view illustrating still another aspect of the graytone part.
Figure 9A:
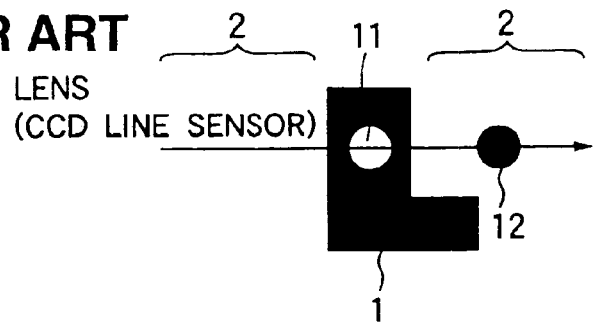
FIG. 9A, FIG. 9B, FIG. 9C, FIG. 9D and FIG. 9E are drawings illustrating a conventional method of defect inspection.
Figure 9B:
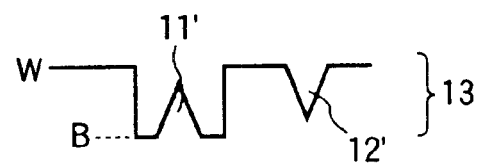
Figure 9C:
Figure 9D:
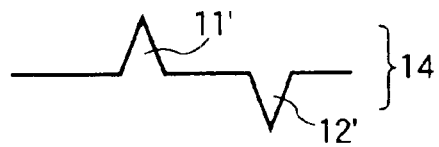
Figure 9E:
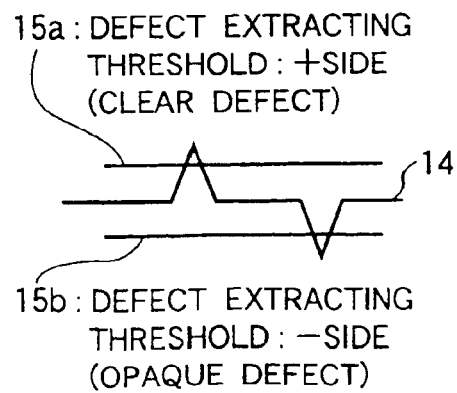

For example, the invention is applicable to cases where the opaque pattern 3a in the graytone part 3 is of a dotted line type as shown in FIG. 7 and where the graytone part 3 is formed of a translucent film 3c as shown in FIG. 8.

Moreover, the method of defect inspection and the apparatus doing the same according to the invention may be combined with the comparative inspection method and device. In this case, the form defect of a pattern can be detected through the comparative inspection simultaneously with the detection of the transmittance defect through the transmittance inspection according to the invention.

Although a description has been given of the inspection of the graytone part of the graytone mask in the embodiment of the invention, the invention is not limited to the embodiment thereof but may be applicable to, for example, photomasks containing microscopic patterns like the graytone parts such as photomasks for forming TFT channels. Even in this case, accurate defect inspection is possible without detecting false defects.

As set forth above, the method of defect inspection of the graytone mask and the apparatus doing the same according to the invention is capable of ensuring the transmittance in the graytone part of the graytone mask.

In particular, the inspection method according to the invention is indispensable for making the graytone mask for the LCD fit for practical use.

Moreover, the method of defect inspection of the photomask allows microscopic patterns of high inspection standard to be accurately (sensitively) inspected.

What is claimed is:

1. A method of defect inspection of a graytone mask, method comprising:

providing a graytone mask having an opaque part, a transmission part and a graytone part, wherein the graytone mask is for selectively varying a thickness of a photoresist film by controlling the amount of light transmitted through each respective part of the graytone mask;

obtaining a transmittance signal by scanning a pattern in the mask;

providing a threshold with respect to the transmittance signal; and determining a transmittance defect in the graytone part in an area where the transmittance signal exceeds the threshold.

2. A method of defect inspection as claimed in claim 1, further comprising:

providing additional thresholds for determining transmittance defects in the respective opaque and transmission parts; and determining that a transmittance defect is produced in the respective opaque and transmission parts when the transmittance signal exceeds each respective threshold.

3. A method of defect inspection as claimed in claim 1, wherein the graytone part is an area wherein a opaque pattern not exceeding the resolution limit of an exposure device using the graytone mask is formed.

4. A method of defect inspection as claimed in claim 1, wherein the graytone part is an area wherein a translucent film capable of controlling the amount of light transmitted through the film is formed.

5. A method of defect inspection as claimed in claim 1, wherein the graytone mask is a mask for producing an LCD or a mask for producing a display device.

6. A method of producing a graytone mask including the step of defect inspection using the method of defect inspection as claimed in claim 1.

7. An apparatus for defect inspection of a graytone mask having a opaque part, a transmission part and a graytone part aimed at selectively varying the thickness of a photoresist film by decreasing the amount of light transmitted through an area wherein the amount of light transmitted therethrough is regulated, the apparatus comprising:

means for detecting a transmittance signal by scanning a pattern formed in the mask with parallel light sources and light receiving lenses, means for setting a threshold for extracting a transmittance defect in at least the graytone part with respect to the transmittance signal, and means for deciding that the transmittance defect is produced in the graytone part in case where the transmission signal exceeds the threshold.

8. A method of defect inspection of a photomask having a microscopic pattern which might cause a problem such that a defect that should be detected by using a comparative inspection method can not be detected appropriately due to influence of a false defect originating from said microscopic pattern, the method comprising:

setting a threshold value for a transmittance signal, wherein the threshold value is variable based on physical properties of the photomask; and detecting a pattern defect in the photomask from an abnormal fluctuation of transmittance based on a comparison of the threshold and a level of a transmittance signal.

9. A method of defect inspection of a photomask as claimed in 8, wherein the photomask is a mask containing a microscopic pattern for producing an LCD or a mask containing a microscopic pattern for producing a display device.

10. A method of producing a graytone mask including the step of defect inspection using the method of defect inspection as claimed in claim 8.

11. A method of defect inspection of a photomask having a microscopic pattern which might cause a problem such that a defect that should be detected by using a comparative inspection method can not be detected appropriately due to influence of a false defect originating from said microscopic pattern, as claimed in claim 8, wherein the detection of the defect from the abnormal fluctuation of transmittance is based on a transmittance-defect threshold set in accordance with a pattern area as an object for inspection.

12. An apparatus for defect inspection of a photomask, comprising:

means for detecting a transmittance signal by scanning a pattern formed in the mask with parallel light sources and light receiving lenses, means for setting a threshold for determining a transmittance defect, wherein a value of the threshold varies based on physical properties of the photomask; and means for deciding that the transmittance defect is produced in the pattern area in case where the transmission signal exceeds the threshold.

* * * * *